United States Patent
Berchoux et al.

(10) Patent No.: US 9,877,757 B2
(45) Date of Patent: Jan. 30, 2018

(54) ARTHROPLASTY PLATE

(71) Applicant: DEPUY (IRELAND), Cork (IE)

(72) Inventors: David Berchoux, Lyons (FR); Sylvain Gauthier, Lyons (FR); Anders Ekelund, Bromma (SE)

(73) Assignee: DEPUY IRELAND UNLIMITED COMPANY, Cork (IE)

( * ) Notice: Subject to any disclaimer, the term of this patent is extended or adjusted under 35 U.S.C. 154(b) by 424 days.

(21) Appl. No.: 14/723,729

(22) Filed: May 28, 2015

(65) Prior Publication Data
US 2015/0272643 A1    Oct. 1, 2015

Related U.S. Application Data

(62) Division of application No. 13/983,582, filed as application No. PCT/EP2012/051526 on Jan. 31, 2012, now Pat. No. 9,066,805.

(30) Foreign Application Priority Data

Feb. 4, 2011 (GB) .................................. 1101896.7

(51) Int. Cl.
  *A61F 2/40* (2006.01)
  *A61B 17/80* (2006.01)
  (Continued)

(52) U.S. Cl.
  CPC .......... *A61B 17/8061* (2013.01); *A61B 17/68* (2013.01); *A61F 2/4003* (2013.01);
  (Continued)

(58) Field of Classification Search
  CPC ...... A61B 17/74; A61F 2/4003; A61F 2/4014; A61F 2/3601; A61F 2002/30474;
  (Continued)

(56) References Cited

U.S. PATENT DOCUMENTS

| 2,381,050 A | 8/1945 | Hardinge |
| 2,397,545 A | 4/1946 | Hardinge |

(Continued)

FOREIGN PATENT DOCUMENTS

| DE | 10123517 C1 | 11/2002 |
| DE | 102006047663 A1 | 4/2008 |

(Continued)

*Primary Examiner* — David H Willse
*Assistant Examiner* — Javier Blanco

(57) ABSTRACT

An arthroplasty plate and method of use to repair a fractured end of a bone are described. The arthroplasty plate comprises a fixation plate arranged to be secured to a surface of a bone and a connector assembly comprising a barrel extending from the fixation plate and having a bore which opens through the fixation plate. A connector rod is arranged to slide within the bore of the barrel. An articulation component comprises a bearing surface coupled to or arranged to couple to an end of the connector rod which extends from the barrel away from the fixation plate. The connector assembly incorporates an adjustment mechanism arranged to cause the connector rod to slide into or out of the barrel and a locking mechanism arranged to lock the position of the connector rod within the barrel to rigidly space the articulation component apart from the fixation plate.

7 Claims, 6 Drawing Sheets

(51) Int. Cl.
*A61B 17/68* (2006.01)
*A61F 2/30* (2006.01)
*A61B 17/74* (2006.01)
*A61F 2/36* (2006.01)

(52) U.S. Cl.
CPC ............ *A61F 2/4014* (2013.01); *A61B 17/74* (2013.01); *A61F 2/3601* (2013.01); *A61F 2002/3055* (2013.01); *A61F 2002/30367* (2013.01); *A61F 2002/30403* (2013.01); *A61F 2002/30433* (2013.01); *A61F 2002/30507* (2013.01); *A61F 2002/30553* (2013.01); *A61F 2002/30601* (2013.01); *A61F 2002/30604* (2013.01); *F04C 2270/041* (2013.01)

(58) Field of Classification Search
CPC .. A61F 2002/30433; A61F 2002/30507; A61F 2002/3055; A61F 2002/30553; A61F 2002/306; A61F 2002/30601; A61F 2002/4037; A61F 2002/4044
USPC ...................................... 623/19.14
See application file for complete search history.

(56) References Cited

U.S. PATENT DOCUMENTS

| | | |
|---|---|---|
| 2,612,159 A | 9/1952 | Collison |
| 3,374,786 A | 3/1968 | Callender, Jr. |
| 3,554,193 A | 1/1971 | Konstantinou |
| 4,005,495 A | 2/1977 | Locke |
| 4,045,825 A | 9/1977 | Stroot |
| 4,101,985 A | 7/1978 | Baumann |
| 4,129,903 A | 12/1978 | Huggler |
| 4,438,762 A | 3/1984 | Kyle |
| 4,612,920 A | 9/1986 | Lower |
| 4,657,001 A | 4/1987 | Fixel |
| 4,686,971 A | 8/1987 | Harris |
| 4,776,329 A | 10/1988 | Treharne |
| 4,791,918 A | 12/1988 | Von Hasselbach |
| 4,795,473 A | 1/1989 | Grimes |
| 4,904,264 A | 2/1990 | Scheunemann |
| 4,976,740 A | 12/1990 | Kleiner |
| 4,998,937 A | 3/1991 | Grimes |
| 5,087,260 A | 2/1992 | Fixel |
| 5,197,989 A | 3/1993 | Hinckfuss |
| 5,376,125 A | 12/1994 | Winkler |
| 5,376,126 A | 12/1994 | Lin |
| 5,569,263 A | 10/1996 | Hein |
| 5,645,607 A | 7/1997 | Hickey |
| 5,658,339 A | 8/1997 | Tronzo |
| 5,725,597 A | 3/1998 | Hwang |
| 5,733,292 A | 3/1998 | Gustilo |
| 5,766,263 A | 6/1998 | Grundei |
| 5,800,553 A | 9/1998 | Albrektsson |
| 5,800,554 A | 9/1998 | Scholz |
| 5,800,557 A | 9/1998 | Elhami |
| 6,139,552 A | 10/2000 | Horiuchi |
| 6,228,120 B1 | 5/2001 | Leonard |
| 6,375,684 B1 | 4/2002 | Kriek |
| 7,097,663 B1 | 8/2006 | Nicol |
| 7,135,023 B2 | 11/2006 | Watkins |
| 7,425,214 B1 | 9/2008 | McCarthy |
| 8,092,466 B2 | 1/2012 | Splieth |
| RE43,482 E | 6/2012 | Mikol |
| 8,968,409 B2 | 3/2015 | Chavarria |
| 2002/0107520 A1 | 8/2002 | Hoffman |
| 2002/0193797 A1 | 12/2002 | Johnson |
| 2003/0028253 A1 | 2/2003 | Stone |
| 2003/0069582 A1 | 4/2003 | Culbert |
| 2003/0187512 A1 | 10/2003 | Frederick |
| 2005/0197712 A1 | 9/2005 | Bigsby |
| 2006/0009852 A1 | 1/2006 | Winslow |
| 2006/0116679 A1 | 6/2006 | Lutz |
| 2006/0200249 A1 | 9/2006 | Beguin |
| 2006/0217720 A1 | 9/2006 | Chieng |
| 2008/0177395 A1 | 7/2008 | Stinnette |
| 2010/0023131 A1 | 1/2010 | Crofford |
| 2010/0331990 A1 | 12/2010 | Mroczkowski |
| 2013/0035761 A1 | 2/2013 | Sharkey |
| 2013/0197652 A1 | 8/2013 | Ekelund |
| 2014/0094855 A1 | 4/2014 | Chavarria |
| 2014/0114425 A1 | 4/2014 | Ekelund |
| 2014/0121709 A1 | 5/2014 | Gonzalez-Hernandez |
| 2014/0121713 A1 | 5/2014 | Meulink |

FOREIGN PATENT DOCUMENTS

| | | |
|---|---|---|
| DE | 102008053566 A1 | 6/2009 |
| EP | 1952788 A1 | 8/2008 |
| FR | 2946863 A1 | 12/2010 |
| GB | 2007980 A | 5/1979 |
| JP | 2004089712 A | 3/2004 |
| WO | WO 1985005027 A1 | 11/1985 |
| WO | WO 1997039693 A1 | 10/1997 |
| WO | WO 2000009038 A2 | 2/2000 |
| WO | WO 2006126238 A2 | 11/2006 |
| WO | WO 2007024980 A2 | 3/2007 |
| WO | WO 2007082925 A2 | 7/2007 |
| WO | WO 2012104285 A1 | 8/2012 |
| WO | WO 2012130517 A1 | 10/2012 |

ARTHROPLASTY PLATE

CROSS REFERENCE TO RELATED APPLICATION

The present application is a divisional of U.S. patent application Ser. No. 13/983,582, filed Jan. 31, 2012 (now granted U.S. Pat. No. 9,066,805, issued Jun. 30, 3015), which is a National Stage 35 U.S.C. 371 of International Patent Application PCT/EP2012/051526 filed Jan. 31, 2012.

The present invention relates generally to orthopaedic surgery. More particularly, the present invention relates to an arthroplasty plate. Specifically, the present invention relates to an arthroplasty plate for repairing fractures of an end of a long bone, which comprises a convex articulation surface forming part of a ball and socket joint. The present invention is particularly suited to the repair of humeral head fractures, although it is not limited to this application.

A natural shoulder joint may undergo degenerative changes for a variety of reasons, for instance arthritis. Alternatively, a shoulder joint may be fractured or otherwise damaged by an external force. When a shoulder joint is sufficiently degenerated or damaged it may be necessary to replace the natural joint with a prosthetic shoulder joint. Conventional shoulder prostheses comprise a humeral prosthesis, optionally with a glenoid prosthesis. For total or reverse arthroplasty a glenoid component is implanted, however for hemi-arthroplasty the humeral component articulates against the natural glenoid cavity.

When the upper extremity of the humerus is fractured, the humerus generally breaks into several pieces, typically three or four. In particular, for "four part fractures" the humeral head splits off at the level of the anatomical neck, the greater and lesser tuberosities are separated from the humerus shaft below the tuberosities and the tuberosities are separated from one another along the bicipetal groove. As there is no longer a blood supply to the humeral head necrosis may begin. For repair of a four-part fracture, or a three part fracture where the blood supply to the humeral head is damaged, the humeral head is replaced, and the greater and lesser tuberosities are reattached to the humeral shaft.

Typically, the humeral component of a shoulder prosthesis comprises a stem for insertion into a bore extending into the intramedullary canal of the humerus, generally along the longitudinal axis of the bone, and an articulation component, which may be a convex bearing head in the case of total arthroplasty or a concave cup in the case of reverse arthroplasty. Typically, the articulation component is coupled to a neck portion of the stem, which extends from the intramedullary canal at an inclined angle relative to the longitudinal axis of a distal portion of the stem in order to recreate the anatomy of the natural joint. Commonly, humeral stem prostheses are secured in position within the intramedullary bore using bone cement. Alternatively, the stem may be coated with a material which encourages bone growth to hold the stem in position, such as Porocoat® or hydroxyapatite. One such humeral stem prosthesis is commercially available from DePuy Orthopaedics, Inc under the trademark Global FX.

For humeral stem prostheses the fractured proximal humerus may fail to heal correctly or healing may be prolonged due to vascular trauma caused by the original injury. Removal of cancellous bone in the intramedullary canal for insertion of the stem, and the heat generated by the cementation, can cause considerable injury to the endosteum of the canal wall. Resulting necrosis of the bone vascularisation inhibits healing of the bone and may even lead to death and resorption of portions of the proximal humerus, especially the greater and lesser tuberosities. Studies have shown that up to one in four humeral stem implants for the repair of humeral fractures have poor results in terms of migration of the tuberosities.

As an alternative to humeral stem implants it is known to repair some types of proximal humeral fracture using an intramedullary nail extending along a bore formed within the intramedullary canal. Screws pass from outside of the humerus, through holes formed within the nail and into the humeral head and the tuberosities. This type of fixation also suffers from vascular damage in the intramedullary canal. Furthermore, a significant drawback is that because the humeral head is not replaced the nail must be inserted through a hole formed in the articular cartilage of the humeral head. A plug must be inserted into the hole to restore the bearing surface.

As a further alternative it is known to repair proximal humeral fractures where the humeral head is relatively undamaged and appears to have an adequate blood flow using a fixation plate attached to the external surface of the proximal humerus. The fixation plate is attached to the lateral surface of the proximal humerus with locking screws. Screws or pegs extend from a head portion of the fixation plate into the humeral head. One such fixation plate is commercially available from DePuy Orthopaedics, Inc under the trademark S3 Shoulder Plate.

For humeral prostheses in which the natural humeral head is replaced with an articulation component, it is important to ensure that the bearing surface is correctly positioned to recreate the natural anatomy of the joint. One option is to provide a range of articulation components each having a different thickness to adjust the height of the bearing surface relative to the humerus. Alternatively, the depth of implantation of the stem into the intramedullary canal may be adjusted. However, it may be difficult to achieve fine control of the position of the bearing head.

For the repair of fractures of the femoral neck it is known to provide a form of prosthesis generally known as a thrust plate prosthesis. One such form of thrust plate prosthesis is disclosed within PCT patent publication WO-2007/024980-A2. The prosthesis comprises a plate portion to be attached to the lateral external surface of the proximal femur. A femoral neck portion comprises an articulation component in the form of a ball coupled to a thrust plate arranged to be seated upon the resected neck of the femur. A tie rod extends from the lateral bone plate to the thrust plate and draws the ball head towards the lateral plate to secure the prosthesis to the bone. The tie rod is tensioned to pre-stress the bone. Under joint loading, force is transferred from the thrust plate to cortical bone within the femoral neck. Alternatively, if the tie rod is not tensioned to compress the femoral neck then force is transferred through the tie rod to the plate. Consequently, some thrust plate prostheses are provided with elongated plate portions to transfer load away from the femoral head and in turn transfer load to intact bone.

It is an object of embodiments of the present invention to obviate or mitigate one or more of the problems of the prior art, whether identified herein or elsewhere.

In particular, it is an object of embodiments of the present invention to provide a humeral reconstruction prosthesis for the surgical repair of a four-part humeral head splitting fracture, or a three-parts humeral head fracture where the blood supply to the head is interrupted. It is a further object of certain embodiments of the present invention to provide a prosthesis which may be implanted without significant vascular trauma of the proximal humerus, thereby promoting faster healing of the fracture.

According to a first aspect of the present invention there is provided an arthroplasty plate comprising: a fixation plate arranged to be secured to a surface of a bone; a connector assembly comprising a barrel extending from the fixation plate with a bore which opens through the fixation plate and a connector rod arranged to slide within the bore of the barrel; and an articulation component comprising a bearing surface coupled to or arranged to couple to an end of the connector rod which extends from the barrel away from the fixation plate; wherein the connector assembly incorporates an adjustment mechanism arranged to cause the connector rod to slide into or out of the barrel and a locking mechanism arranged to lock the position of the connector rod within the barrel to rigidly space the articulation component apart from the fixation plate.

An advantage of the present invention is that because the distance between the articulation component and the fixation plate can be varied, the height of the articulation component above the end of the bone may be adjusted. Consequently, when the arthroplasty plate forms part of a shoulder prosthesis, the tension in the shoulder joint when the joint is reduced (created by ligaments and other soft tissue extending from the scapula to the humerus) may be adjusted by varying the geometry of the joint in order to allow for natural movement of the joint and to reduce the risk of further injury to the joint. As a fractured humeral head is typically split into a number of portions, it may be undesirable to transfer load directly from a replacement articulation component onto cortical bone in the humeral head.

An arthroplasty plate in accordance with the present invention allows the surgeon to space the articulation component apart from the end of the bone so that the fractured bone is not compressed. Load is transferred from the articulation component to the plate, which is secured to the bone further along the humerus where the bone is intact. A further advantage is that the amount of disruption to the vasculature of the proximal humerus is minimised, compared with a humeral stem implant. Furthermore, because the proportion of bone that is removed is minimised, revision surgery may be performed more readily in the event of failure of the implanted prosthesis.

The connector rod and the bore of the barrel may have corresponding engaging features to prevent the connector rod from rotating within the barrel. The corresponding engaging features may comprise a boss extending from one of the connector rod or the barrel arranged to slidably engage a groove formed within the other of the connector rod and the barrel extending parallel to the axis of the barrel The adjustment mechanism may comprise an adjustment sleeve rotatably disposed within the barrel and couplable to the connector rod through corresponding screw threads upon the adjustment sleeve and the connector rod such that rotating the adjustment sleeve relative to the connector rod causes the connector rod to slide relative into or out of the barrel to adjust the distance between the articulation component and the fixation plate.

The locking mechanism may comprise a locking screw arranged to pass through the adjustment sleeve and to be received within a bore formed within the connector rod and couplable to the connector rod through corresponding screw threads such that screwing the locking screw into the connector rod bore prevents further movement between the adjustment sleeve and the connector rod.

The bore of the barrel may further comprise an annular flange, the adjustment sleeve may comprise a head portion located on a first side of the flange and the locking screw may comprise a head portion, wherein when the locking screw engages the connector rod bore the annular flange may be positioned between the head portions of the adjustment sleeve and the locking screw. The head portions of the adjustment sleeve and the locking screw may both comprise sockets arranged to separately receive a tip of a driver to separately rotate the adjustment sleeve and the locking screw.

The fixation plate may comprise a head portion couplable to the connector assembly and an elongate body portion arranged to extend distally along the lateral surface of the bone, the elongate body portion comprising a plurality of fastener holes arranged to receive bone fasteners for securing the fixation plate to the bone. The elongate body portion may further comprise an elongate slot arranged to receive a bone fastener such that the fixation plate can slide along the surface of the bone. The fixation plate head portion may comprise at least one suture hole for securing bone fragments and soft tissues to the fixation plate.

According to a second aspect of the present invention there is provided a method of repairing a fractured end of a bone, the method comprising: removing fractured portions of an articulating bone surface at the end of the bone; securing a fixation plate to a lateral surface of the fractured end of the bone, the fixation plate being coupled to a connector assembly comprising a barrel with a bore and a connector rod arranged to slide within the bore of the barrel the bore of the barrel opening through the fixation plate, an articulation component comprising a bearing surface being coupled to or arranged to couple to an end of the connector rod which extends from the barrel away from the fixation plate; sliding the connector rod into or out of the barrel to adjust the length of the connector rod extending from the barrel; and locking the position of the connector rod within the barrel to rigidly space the articulation component apart from the fixation plate.

The method may further comprise: reducing the joint at the end of the bone; releasing the locking mechanism; and adjusting the length of the connector assembly using the length adjusting mechanism to vary the tension within the joint.

In a further embodiment there is provided an arthroplasty plate comprising: a fixation plate arranged to be secured to a surface of a bone; a connector assembly having a first end arranged to couple to the fixation plate and a second end arranged to couple to an articulation component to secure the articulation component to the fixation plate; wherein the connector assembly incorporates a length adjustment mechanism arranged to vary the distance between the second end of the connector assembly and the fixation plate such that the position of the articulation component relative to the end of the bone can be adjusted.

In a further embodiment there is provided a method of repairing a fractured end of a bone, the method comprising: resecting the end of the bone to remove an articulating bone surface or removing fractured portions of the articulating bone surface; attaching a fixation plate to a lateral surface of the proximal portion of the bone, the fixation plate being couple to a connector assembly extending towards the position of the articulating surface of the bone; and adjusting the length of the connector assembly using a length adjusting mechanism; wherein adjusting the length of the connector assembly adjusts the position of the articulation component relative to the end of the bone.

The present invention will now be described, by way of example only, with reference to the accompanying drawings, in which.

Figure 1:
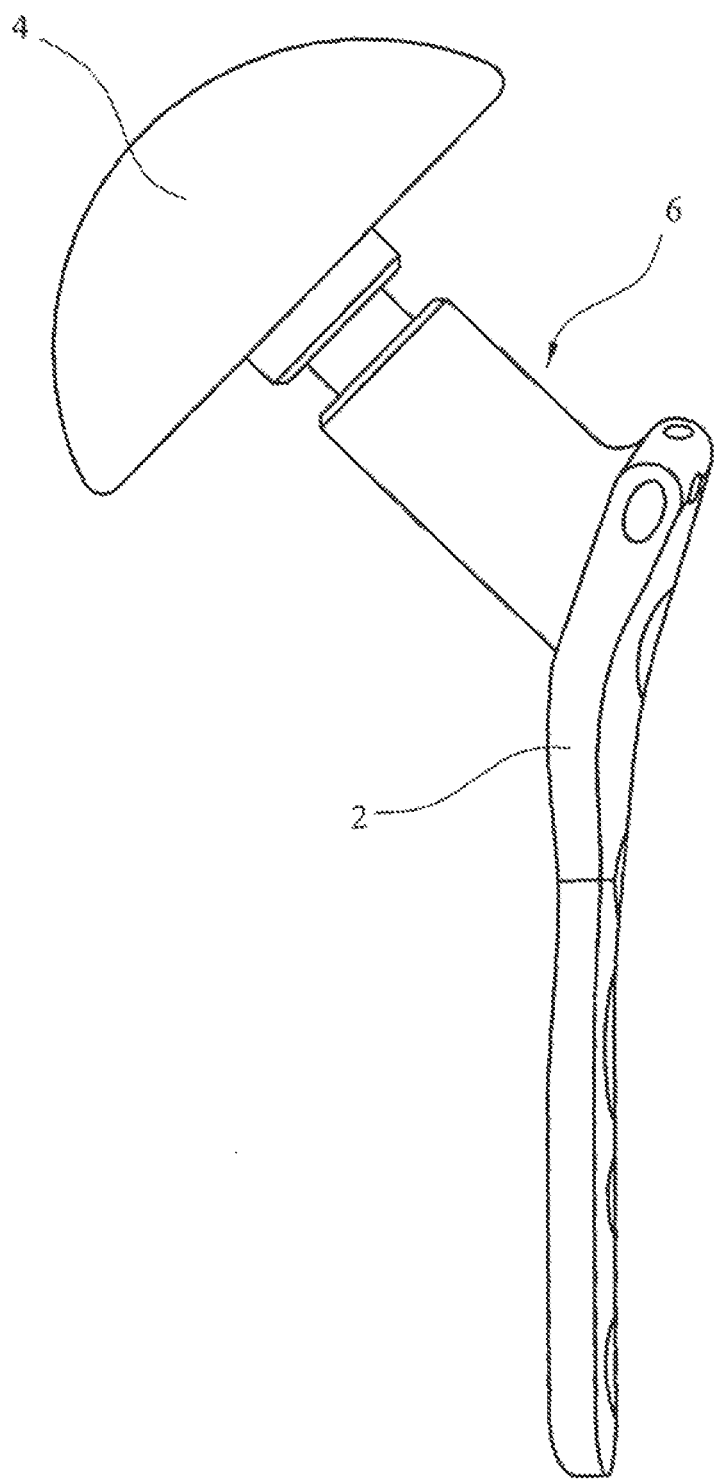
FIG. 1 is a view in a frontal plane of an arthroplasty plate prosthesis according to an embodiment of the present invention coupled to an articulation component.

Referring first to FIG. 1, this is a view in a frontal plane of an assembled arthroplasty plate for repair of a fractured proximal humerus in accordance with an embodiment of the present invention. The arthroplasty plate comprises a fixation plate 2 for attachment to a lateral external portion of a proximal humerus of a patient. An articulation component 4 replaces the natural humeral head. The articulation component 4 comprises a convex bearing surface and is sized and shaped to articulate with either the natural glenoid surface or an implanted glenoid prosthesis to reconstruct the shoulder joint. The articulation component 4 is coupled to the fixation plate 2 via a connector assembly 6 positioned in a bore formed in the proximal humerus.

Figure 2:
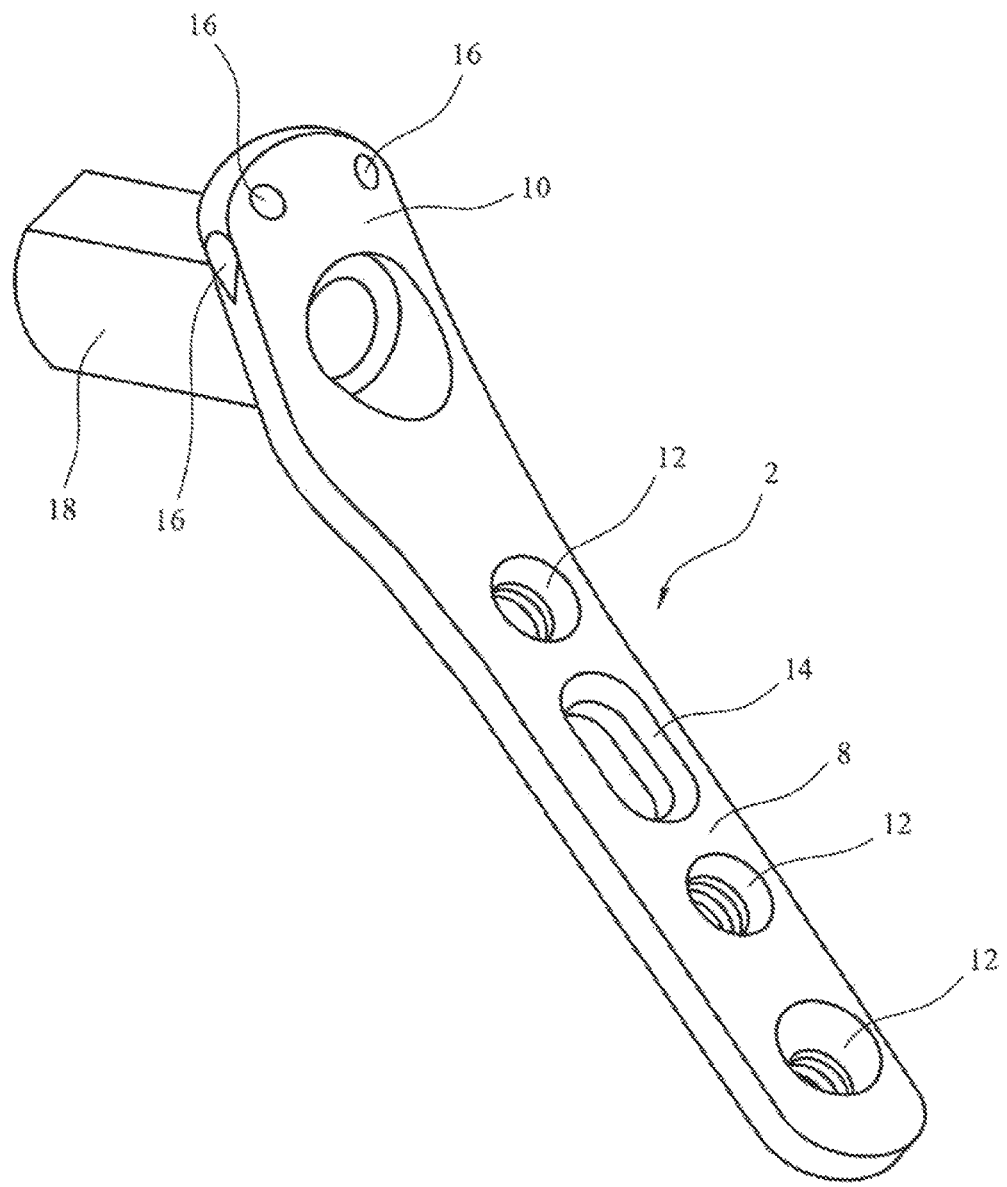
FIG. 2 is a perspective view of the plate portion of the prosthesis of FIG. 1.

The fixation plate 2 is illustrated in a perspective view in FIG. 2. The fixation plate 2 comprises an elongate body portion 8 and a head portion 10 arranged to conform to the surface of the lateral humerus. The body portion 8 incorporates a number of screw holes 12 for securing the plate 2 to the humerus. The axes of the screw holes 12 may diverge as they enter the bone in order to reduce the possibility of the plate 2 pulling away from the bone. In particular, the axes of two of the screw holes 12 may enter the bone transverse to the plate of the body portion 8 and the axis of the distal-most screw hole 12 may extend obliquely into the bone. The screw holes 12 may be threaded to receive the threaded head of a fixed angle bone screw or a locking screw. The thread of the screw hole 12 defines the axis of the screw hole. Alternatively, or in addition, the screw holes may be arranged to receive variable axis bone screws. The holes 12 may also receive smooth pegs or fully or partially threaded pegs. More generally, any known form of fastener may be used to couple the plate 2 to the bone.

A slotted screw hole 14 is provided for initial fixation of the plate 2 to the bone. A screw is inserted into the bone through slotted hole 14 allowing the plate 2 to slide along the bone before the fixation plate 2 is permanently attached. Suture holes 16 are provided about the head portion 10 for securing soft tissues and bone fragments to the fixation plate 2.

The plate 2 further comprises an integrally formed hollow barrel 18 extending from the plate transverse to the longitudinal axis of the plate, for instance at 135°. The angle at which the barrel 18 extends is chosen to recreate the natural anatomy of the proximal humerus by positioning the articulation component in the correct anatomical position, as will be described below. The barrel 18 is inserted into a bore formed in the proximal humerus extending from the lateral bone surface to the resected humeral head. The barrel 18 forms part of the connector assembly 6 as will be described below in connection with FIG. 3. The barrel 18 may be covered with a porous material such as Porocoat® in order to encourage bone ingrowth, which assists the fixation of the plate 2 to the bone.

Figure 3:
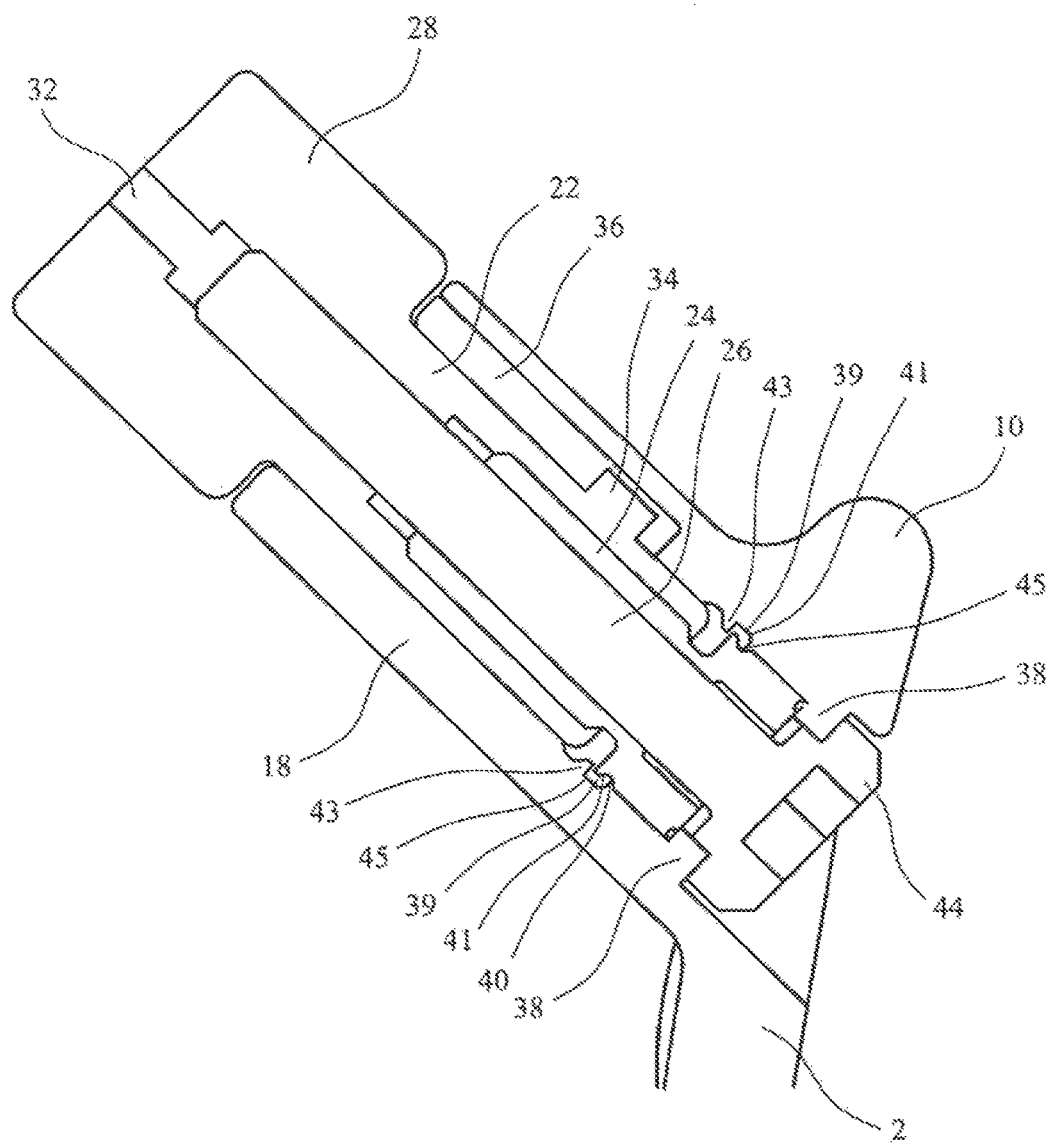
FIG. 3 is a cross sectional view of the connector assembly of the prosthesis of FIG. 1 extending in the same plane as the view of FIG. 1.

Referring now to FIG. 3, this illustrates a cross sectional view of the connector assembly of the arthroplasty plate of FIG. 1 to better illustrate details of the connector assembly 6. The connector assembly 6 couples the articulation component 4 to the plate 2. The connector assembly 6 is adjustable in length to allow the surgeon to adjust the relative position of the articulation component 4. Specifically, the connector assembly 6 adjusts the position of the centre of the taper 28 such that when coupled to an articulation component 4 the convex bearing surface 20 may be shifted towards or away from the plate 2 in order to adjust the tension in the reduced shoulder joint without requiring multiple separate articulation components of different thicknesses. Furthermore, owing to the way in which the connector assembly 6 is adjusted, the spacing between the articulation component 4 and the plate 2 can be adjusted when the shoulder joint is reduced, without requiring the joint to be dislocated to replace the articulation component, as will now be explained.

Figure 4:
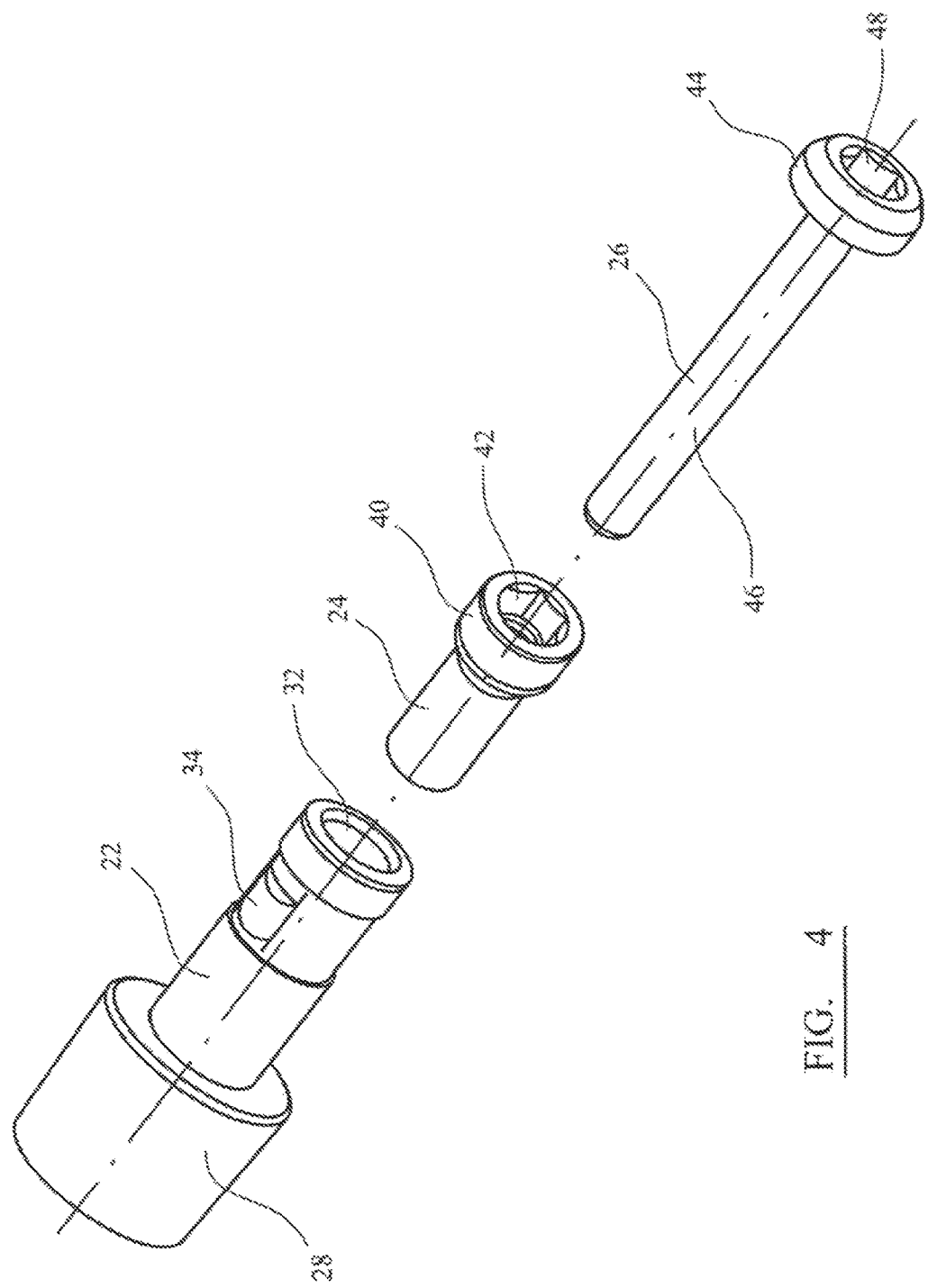
FIG. 4 is an exploded view of portions of the connector assembly of the prosthesis of FIG. 1.

The connection assembly 6 comprises barrel 18 (forming part of the plate 2), a connector rod 22 coupled at a first end to the articulation component 4, an adjustment sleeve 24 and a locking screw 26. The connector rod 22, adjustment sleeve 24 and locking screw 26 are also illustrated in an exploded view in FIG. 4.

The first end of connector rod 22 comprises a frustoconical taper 28 arranged to be received in and locked to a tapered bore within the reverse side of the articulation component 4. The form of taper 28 may be generally the same as is known for existing humeral stem prosthesis for coupling an articulation component to a neck portion of the prosthesis, and so will not be further described here. A smooth bore 32 extends along the length of the connector rod 22 to receive the locking screw 26. The second end of the connector rod 22 is slidably received within the tubular barrel 18. Rotation between connector rod 22 and barrel 18 is limited by an anti-rotation boss 34 extending from one side of the connector rod 22 and slidably received within a groove 36 extending axially within tubular barrel 18.

The bore of barrel 18 comprises an annular flange 38 arranged to prevent the adjustment sleeve 24 from passing out of the barrel 18 away from the articulation component 4. The head 40 of adjustment sleeve 24 fits within the bore of barrel 18 and can rotate within the barrel 18. The head 40 of the adjustment screw 24 further comprises an annular flange 39 and groove 41. The annular flange 39 protrudes slightly beyond the circumference of the remainder of head 40. The side of the flange 39 adjacent to the groove 41 is chamfered. The interior of the barrel 18 also comprises a second flange 43 and groove 45. The side of flange 43 facing away from the plate 2 is chamfered. Flange 43 extends further into the bore of the barrel than adjacent portions of the barrel wall.

Flanges 39 and 43 interact such that during assembly of the connector assembly, when the adjustment sleeve 24 is inserted into the barrel 18 flanges 39 and 43 slightly deform to allow the head 40 of the adjustment sleeve 24 to be fully inserted into the barrel. The deformation is assisted by the chamfered edges of the flanges. The overlap between the flanges is suitably small, for instance 0.1 mm, to allow the flanges to temporarily deform and then revert to their former shape. The deformation is assisted by the chamfered sides to the flanges sliding over one another. Consequently, if an attempt is made to pull the adjustment sleeve 24 from the barrel, a greater force is required than that required to insert the adjustment sleeve 24 into the barrel, thereby retaining the adjustment sleeve 24 within the barrel 18. A socket 42 illustrated in FIG. 4, for instance a hexagonal socket, is formed in the head 40 of adjustment sleeve 24 and is arranged to receive an end of a screwdriver (not shown) for rotating the adjustment sleeve 24 within barrel 18.

Extending away from head 40, the adjustment sleeve 24 is tubular with an exterior dimension arranged to be received within the bore 32 within connector rod 22. An exterior screw thread is formed upon the outside of adjustment sleeve 24 and arranged to engage an interior screw thread within bore 32 such that when adjustment sleeve 24 is rotated relative to connector rod 22, connector rod 22 slides into or out from barrel 18.

Locking screw 26 comprises a head portion 44 and a shaft portion 46. An exterior screw thread is formed upon locking screw 26 remote from head 44 and is arranged to engage a screw thread formed in a narrowed portion of bore 32 within connector rod 22.

The head portion 44 of locking screw 26 is arranged to abut the flange 38 within barrel 18 such that when the connector assembly 6 is assembled the flange 38 is trapped between head 44 of the locking screw 26 and head 40 of the adjustment sleeve 24. A socket 48, for instance a hexagonal socket, is formed in the head 44 of locking screw 26 and is arranged to receive an end of a screwdriver (not shown) for rotating the locking screw 26 within barrel 18. Preferably socket 48 is arranged to receive the same screwdriver as the socket 42 formed within the head of the adjustment sleeve 24.

The length of the connector assembly 6 may be adjusted by rotating adjustment sleeve 24 within barrel 18 such that it screws into or out from bore 32 in connector rod 22 causing the connector rod 22 to slide into or out from barrel 18. Once the correct length has been achieved locking screw 26 is inserted through adjustment sleeve 24 into connector rod 22 and tightened to draw the connector rod 22 towards the plate 2 until locking screw 26 rests upon the flange 38, thus preventing micro-movement between the connector rod 22, the adjustment sleeve 24 and the plate 2. This adjustment may be performed before or after the articulation component 4 has been coupled to the connector rod 22.

Advantageously, the connector assembly 6 may be used to adjust the distance between the articulation component 4 and the plate 2 so as to adjust tension within the reduced joint. Furthermore, the connector assembly may be adjusted to allow the reverse surface of the articulation component 4 to rest upon fragments of the tuberosities within the humeral head if direct load transfer to the bone is required. Alternatively, the articulation component 4 may be slightly spaced apart from the bone if the bone in the humeral head is badly fractured such that load applied to the shoulder joint is transmitted from the articulation component 4, through the connector assembly 6 and through plate 2. Plate 2 extends along the humerus sufficiently far to ensure that it can be secured to intact bone.

Figure 5:
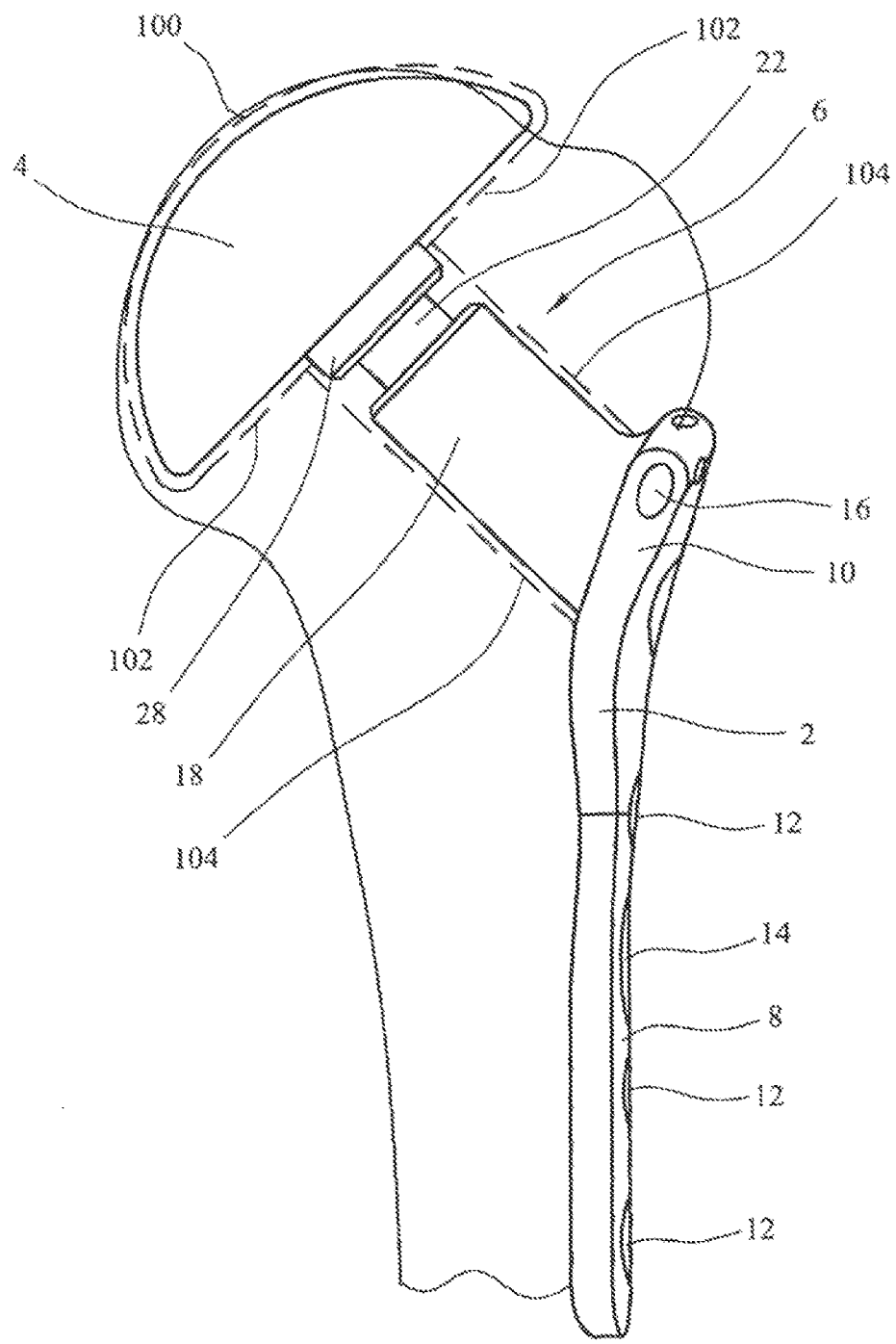
FIG. 5 is a partial cross sectional view in a frontal plane of the arthroplasty plate prosthesis and articulation component of FIG. 1 coupled to a bone.

Referring now to FIG. 5, the arthroplasty plate prosthesis and articulation component of FIG. 1 are illustrated in a partial cross sectional view in a frontal plane coupled to a humeral head. In particular, portions of the bone overlying the arthroplasty plate prosthesis are omitted to allow the whole prosthesis to be seen. Furthermore, those portions of the head of the humerus that are removed during the implantation of the prosthesis (the articulation surface and bone within the bore) are shown in phantom.

A surgical procedure for implanting the arthroplasty plate prosthesis to repair a fractured humeral head will now be described. It will be appreciated that details of the surgical procedure may vary, for instance according to the preferences of the surgeon. As discussed above, the arthroplasty plate prosthesis of embodiments of the present invention may be indicated for repair of three-part or four-part proximal humeral fractures. In a four-part proximal humeral fracture the humeral head is a free fragment not coupled to any soft tissue and deprived of a blood supply. The greater and lesser tuberosities are detached. The greater tuberosity is displaced superiorly and posteriorly by the attached rotator cuff, while the lesser tuberosity is retracted medially by the attached subscapularis. The fractured end of the humeral shaft is displaced medially by the pull of the pectoralis major. Three-part fractures differ in that the lesser or greater tuberosity remains attached to the humeral head, which in consequence is rotated internally by the subscapularis tendon.

The surgeon must first gain access to the fractured humeral head. The patient must be positioned so as to allow the surgeon free access to the injured shoulder, for instance in a "beach chair" position, with the injured arm hanging free, providing space for later manipulation of the arm. The fracture may be examined using fluoroscopy, including under internal and external rotation. A deltopectoral exposure may be used to identify the coracoid, acromium and deltoid insertion. The interval between the pectoralis and the deltoid is developed and the incision line is extended distally from the coracoids.

The exposure is through a 12-14 cm incision. The incision may be held open using self retaining retractors. Care must be taken to identify and retract the cephalic vein. The coracobrachialis is retracted medially and the pectoralis insertion at the floor of the deltopectoral interval is located allowing the subacromial space to be developed to mobilise the proximal deltoid.

The detached humeral head may then be removed (after releasing the head from the lesser or greater tuberosity in the case of a three-part fracture). The appropriate size of articulation component 4 may then be chosen, for instance by comparing the humeral head to a gauge to measure its height and radius of curvature. The tuberosities are also released from underlying soft tissues, taking care to protect the axillary nerve when mobilising the lesser tuberosity and the attached subscapularis muscle tendon. The tuberosities are released so as to allow them to be coupled to each other and to the arthroplasty plate, passing around the prosthesis.

Figure 6:
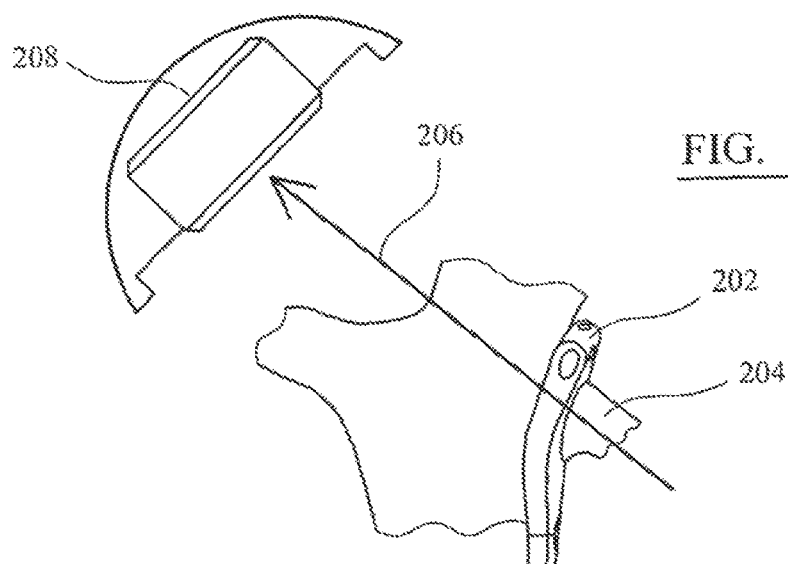
FIG. 6 illustrates a trial plate coupled to a bone.

A trial plate 200 is then applied to the surface of the humerus as illustrated in FIG. 6. The trial plate 200 is generally the same as the prosthesis plate 2, and in particular the bone contacting surface is of the same form. However, the trial plate 200 does not include a barrel 18 and so it may be freely positioned over the surface of the humerus. Traction of the arm may be required to hold the trial plate 200 at the correct height. Additionally the arm may require to be internally rotated such that the articulation component (when positioned) is directed into the glenoid fossa. The trial plate 200 is available in left and right arm versions, as is the prosthesis. The anterior side of the trial plate is aligned with the bicipetal groove. A trial plate handle (not illustrated) may be provided coupling to a head portion 202 of the trial plate 200. The trial plate handle assists in manoeuvring the trial plate 200. Furthermore, the trial plate handle is arranged to extend from the trial plate 200 such that when aligned with the forearm (with the elbow bent at approximately 90°) the trial head will be positioned with 30° of retroversion (though this may be varied according to clinical indications.

The trial plate 200 further comprises a guide 204 arranged to guide a 2 mm guide wire. The guide wire indicates where the prosthetic head (articulation component 4) will be centred.

The guide wire extends along the axis indicated by arrow 206. This allows the surgeon to see that the trial head will be in the correct position in relation to the calcar region and the tuberosities. The guide wire is advanced slowly and the trajectory may be verified under fluoroscopy. The guide wire serves to temporarily secure the trial plate 200 to the bone and to verify the alignment of connector rod 22 of the prosthesis. A trial head 208 is coupled to the guide wire. When correctly positioned the inferior aspect of the trial head 208 should align with the medial end of the humeral head.

Once the position of the trial head has been confirmed, the surgeon may be required to remove remaining fragments of the articulation surface 100 of the humeral head (shown in phantom in FIG. 5). Typically, the articulation surface 100 may already be fractured or detached from the humerus requiring the surgeon to perform a resection to provide a resected surface 102 (shown in phantom in FIG. 5) to later support or be spaced apart from the articulation component 4.

A drill reamer (not illustrated) is then used to form the bore 104 to receive the barrel 18. bore 104 is shown in phantom in FIG. 5. The drill reamer is guided by guide 204. The bore 104 extends generally normal to the resected surface 102 through the humeral head to the lateral humeral surface. The fixation plate 2 may then be secured to the lateral humeral surface, the connector assembly 6 being inserted into the bore 104. The trial head 208 may be temporarily coupled to the plate 2 to check the final position of the neck axis. The fixation plate 2 is secured initially by passing a screw through the slotted screw hole 14 which allows the fixation plate 2 to slide along the lateral humeral surface. The fixation plate 2 is then secured in position by passing screws through the remaining screw holes 12. The plate 2 may be fixed with locking or non-locking screws. A locking screw is recommended for the distal angulated hole fixation. Non-locking screws should be inserted first to pull the plate to the bone.

The articulation component 4 is then secured to the taper 28. The position of the articulation component 4 may then be adjusted by adjusting the length of the connector assembly 6 (that is the distance between the centre of taper 28 and the fixation plate 2) by rotating adjustment sleeve 24. The position of the articulation component may either be determined before or after the shoulder joint is reduced, or further adjustment may be performed after the shoulder joint is reduced. The articulation component 4 is then locked in position by passing locking screw 26 through the barrel 18 and the adjustment sleeve 24 to engage the taper 28.

Figure 7:
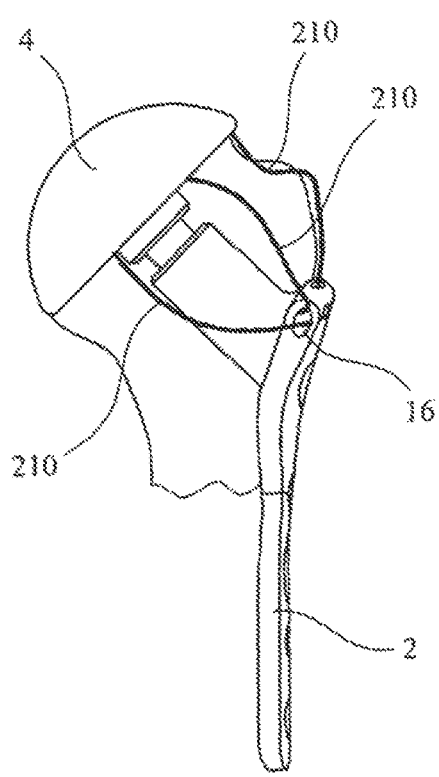
FIG. 7 illustrates the use of sutures to secure bone fragments to the arthroplasty plate.
Figure 8:
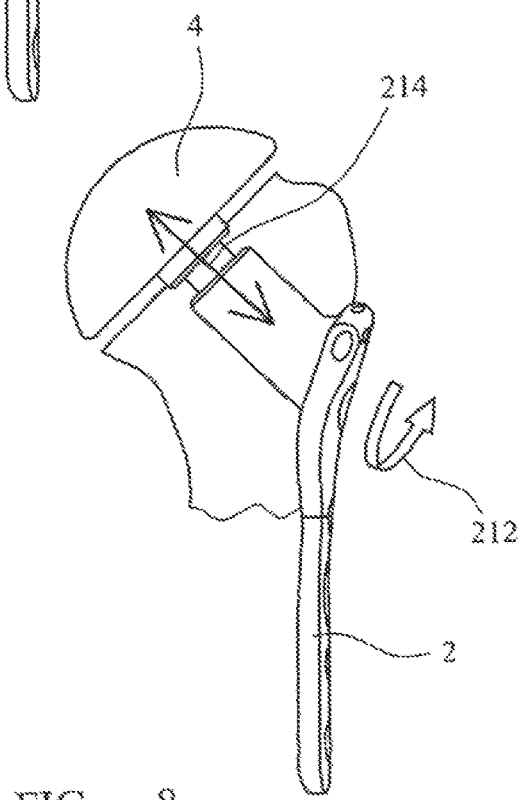
FIG. 8 illustrates adjustment of the height of an articulation component in accordance with an embodiment of the present invention.

Loose fragments of bone or soft tissue are secured to the arthroplasty plate using sutures secured to suture holes 16. In particular the greater and lesser tuberosities are secured to the suture holes and around the arthroplasty plate. As the sutures may pull through tuberosity fragments in osteoporotic bone, preferably the sutures are additionally or only passed through the cuff tendons. Sutures 210 may also couple holes in the articulation component 4 to the suture holes 16 as illustrated in FIG. 7 so as to pass over the tuberosities and secure them to the prosthesis. Compression, if required, between the articulation component 4 and the tuberosities may be provided by rotating the adjustment sleeve 24, as illustrated by arrow 212 in FIG. 8. Movement of the articulation component 4 relative to the plate 2 in the direction of arrow 214 also serves to tension sutures 210.

Owing to the relatively small dimensions of the humeral head, the present inventors have realised that a connector assembly that is adjustable in length may be provided because the lever arm between the articulation component and the plate is short enough to minimise any risk of damage to the connector assembly under loading. For femoral prostheses, due to the larger distance between the femoral head and the lateral femoral bone surface, an adjustable connector assembly would be more difficult to safely achieve owing to the larger bending force that would be applied to the connector assembly (especially taking into account the greater load that is typically applied to a hip joint relative to a shoulder joint).

Although as noted above it is not necessary to provide a range of articulation components with different thicknesses in order to adjust the shoulder tension for a particular patient, it may still be necessary to provide a range of different sized articulation components to account for differences in anatomy between patients. Similarly, the fixation plate and connector assemblies may be provided in a range of sizes, and in the case of the fixation plate in left and right handed versions. Specifically, the plate may be asymmetrical to account for differences between the left and right humerus.

Furthermore, the proximal portion of the fixation plate may be widened to extend over one or both of the tuberosities. The head of the plate is intended to conform closely to the shape of the proximal humerus. In particular, the head of the plate may be angled with respect to the body portion to conform to the lateral proximal surface of the humerus. Suture holes are provided within the head of the plate for reattaching bone fragments and soft tissues to the repaired humerus. The plate may also comprise multifunctional holes for attaching sutures or for receiving provisional fixation pins or guide wires.

As described above, in the illustrated embodiment of the present invention the connector rod is a separate component to the articulation component. However, it will be appreciated that the connector rod may be integrally formed with the articulation component. Either way, the connector rod preferably extends from the articulation component at a fixed angle. Most preferably, the convex bearing surface is defined by a portion of a sphere and the connector rod extends along the polar axis of the bearing surface. Similarly, the barrel has been described as being integrally formed with the plate, however this need not necessarily be the case. The barrel may be a separate component that couples to the plate using a screw thread or a camming mechanism.

A particular form of length adjustment mechanism for a connector assembly has been described. However, the details of the connector assembly are merely exemplary and represent the currently contemplated form of the assembly. The invention is not limited to details of the connector assembly, rather it extends to any mechanism for adjusting the spacing between an articulation component and a plate coupled to the proximal lateral portion of a bone, where the mechanism extends through a bore passing through the bone.

The present invention has been primarily described above as forming part of a shoulder prosthesis. The arthroplasty plate is particularly suitable for the repair of shoulder fractures because the fixation plate extends along the length of the humerus until intact bone is encountered to ensure good fixation. However, the arthroplasty plate may also form part of a femoral prosthesis for the repair of hip fractures.

Other modifications to, and applications of, the present invention will be readily apparent from the teaching herein without departing from the scope of the appended claims.

The invention claimed is:

1. A method of repairing a fractured end of a humerus, the method comprising:
    removing fractured portions of an articulating bone surface at the end of the humerus;
    using a shoulder prosthesis, the shoulder prosthesis comprising:
        a fixation plate comprising an elongate body portion arranged to extend distally along the lateral external surface of the humerus, the elongate body portion having a lateral side with a proximal opening formed thereon and a plurality of fastener holes arranged to receive bone fasteners for securing the fixation plate to the bone;
        a tubular barrel integrally formed with and extending from the fixation plate, the barrel configured to be inserted into a bore formed in the proximal humerus extending from a lateral bone surface to a resected humeral head, the barrel having an axis and a barrel bore, the barrel bore communicating with the proximal opening in the fixation plate;
        a connector rod having a first end and a second end, the second end being slidable within the barrel bore, the connector rod having a connector bore extending therethrough;
        an articulation component having a bearing surface, the articulation component coupled to the first end of the connector rod and away from the fixation plate;
        a tubular adjustment sleeve rotatably and entirely disposed within the barrel, the adjustment sleeve having a first end with an exterior screw thread, a second end defining a sleeve head portion, and an adjustment sleeve bore extending therethrough, the first end of the adjustment sleeve being threadably coupled to the connector bore of the connector rod, the adjustment sleeve rotatable between a first position, whereat the first end of the connector rod is a first distance as measured from the lateral side of the fixation plate, to a second position, whereat the first end of the connector rod is a second distance as measured from the lateral side of the fixation plate, the second distance being greater than the first distance; and
        a locking screw disposed within the adjustment sleeve bore and threadably coupled to the connector rod, the locking screw comprising a screw head portion,
    wherein the barrel includes an inner surface that forms the barrel bore, the barrel comprises an annular flange formed on the inner surface and adjacent to the opening formed on the lateral side of the fixation plate, the annular flange extending from the inner surface toward the axis of the barrel and defining a first side and a second side, the sleeve head portion disposed on the first side of the annular flange and the screw head portion disposed on the second side of the annular flange, and wherein when the locking screw engages the connector rod bore the annular flange is positioned between the sleeve head portion and the screw head portion;
    securing said fixation plate to the lateral external surface of the humerus;
    sliding the second end of the connector rod into or out of the barrel to adjust the length of the connector rod extending from the barrel; and
    locking the position of the connector rod within the barrel to rigidly space the articulation component apart from the fixation plate by screwing said locking screw into the connector bore to prevent further movement between the adjustment sleeve and the connector rod.

2. The method according to claim 1, further comprising:
    reducing the joint at the end of the humerus;
    releasing the locked position of the connector rod; and
    adjusting the length of the connector rod extending from the barrel to vary the tension within the joint.

3. The method according to claim 1, wherein the connector rod and the bore of the barrel have corresponding engaging features to prevent the connector rod from rotating within the barrel.

4. The method according to claim 3, wherein the corresponding engaging features comprises a boss extending from one of the connector rod or the barrel arranged to slidably engage a groove formed within the other of the connector rod and the barrel extending parallel to the axis of the barrel.

5. The method according to claim 1, wherein the method further includes rotating the adjustment sleeve relative to the connector rod, which causes the connector rod to slide relative into or out of the barrel to adjust the distance between the articulation component and the fixation plate.

6. The method according to claim 1, wherein the method further including securing the fixation plate to the lateral external surface of the humerus using said plurality of fastener holes arranged on the elongate body portion.

7. The method according to claim 6, further comprising securing bone fragments and soft tissue to the fixation plate via at least one suture hole in the elongate body portion.

* * * * *